United States Patent [19]

Houng et al.

[11] Patent Number: 5,552,317

[45] Date of Patent: Sep. 3, 1996

[54] METHOD FOR PREPARING OPTICALLY ACTIVE HOMOPHENYLALANINE AND ESTERS THEREOF USING LIPASE FROM WHEAT GERM OR *CANDIDA LIPOLYTICA*

[75] Inventors: Jer-Yiing Houng; Chung-Lung Hsieh, both of Hsinchu, Taiwan

[73] Assignee: Industrial Technology Research Institute, Hsinchu Hsien, Taiwan

[21] Appl. No.: 451,602

[22] Filed: May 26, 1995

[51] Int. Cl.$^6$ .................................................. C12P 41/00
[52] U.S. Cl. ............................................................. 435/280
[58] Field of Search ............................................. 435/280

[56] References Cited

U.S. PATENT DOCUMENTS 5,219,731  6/1993  Sih ............................................ 435/18

FOREIGN PATENT DOCUMENTS

| 0310012 | 9/1988 | European Pat. Off. . |
| 63-63646 | 3/1988 | Japan . |
| 63-145256 | 6/1988 | Japan . |
| 6479133 | 3/1989 | Japan . |
| 1320991 | 12/1989 | Japan . |
| 2276586 | 11/1990 | Japan . |

OTHER PUBLICATIONS

Kosui N et al., Mem. Fac. Sci, Kyushu Univ., Ser. C 13 (1):89–96 (1981).
Chen S–T et al., Chirality 6 (7):572–6 (1994).
Chi–Huey Wong et al., Enzymes in Organic Synthesis; Use of Subtilisin and a Highly Stable Mutant Derived from Multiple Site–Specific Mutations/J. Am. Chem. Soc. 1990, 112, 945–953.
Aih–Jing Chiou et al., Enantioselective Hydrolysis Of Hydrophobic Amino Acid Derivatives By Lipases/Biotechnology Letters, vol. 14 No. 6 (Jun. 1992) pp. 461–464.
Toshifumi Miyazawa et al., Porcine Pancreatic Lipase Catalyzed Enantioselective Hydrolysis of Esters of N–Protected Unusual Amino Acids/Chemistry Letters, pp. 2219–2222, 1989. The Chemical Society of Japan.
Shui–Tein Chen et al., Kinetic Resolution Of N–Protected Amino Acid Esters In Organic Solvents Catalyzed By A Stable Industrial Alkaline Protease/ Biotechnology Letters vol. 13, No. 11, 773–778 (1991).
Tsung–Chin Tseng et al., Enantioselective Synthesis of N–[(S)–Ethoxycarbonyl–3–Phenylpropyl]–L–alanyl–L––proline from Chiral Synthon Prepared Enzymatically; A Pratical Method for Large–Scale Synthesis/Journal of the Chinese Chemical Society, 1991,38, 487–490.
Christoph Syldatk et al., Biotechnological Production Of Unnatural L–Amino Acids From D, L–5–Monosubstituted Hydantoins. II. L–α–and L–β–Naphthylalanine/Biotechnology Letters vol. 14 No. 2 (Feb. 1992) pp. 105–110.
Tatsuro Kijima et al., Facile Optical Resolution of Amino Acid Esters via Hydrolysis by an Industrial Enzyme in Organic Solvents/J. Chem. Tech. Biotechnol. 1994, 59, 61–65.

*Primary Examiner*—David M. Naff
*Assistant Examiner*—S. Saucier
*Attorney, Agent, or Firm*—W. Wayne Liauh

[57] ABSTRACT

A process for the preparation of optically active D-homophenylalanine and its esters, comprising the steps of: (a) preparing a reaction mixture containing an DL-homophenylalanine ester and a lipase or an acylase in an aqueous solution; (b) reacting the reaction mixture at temperatures between 4° and 60° C.; and (c) using an organic extractant to separate the reaction mixture into an upper layer, which contains an optically active D-homophenylalanine ester, and a lower layer, which contains L-homophenylalanine. The optically active D-homophenylalanine ester can be chemically hydrolyzed to obtain an optically active D-homophenylalanine. The lipase can be selected from the group consisting of *Aspergillus niger* lipase, Pseudomonas sp. lipase, Rhizopus sp. lipase, porvine pancreas lipase, wheat germ lipase, and hog pancreas lipase, and the acylase can be porcine kidney acylase. Many of these lipases or acylase provide an enantiometric excess of more than 95%. The optically active D-homophenylalanine is an important starting material for many anti-hypertensive drugs, such as Enalapril, Lisinopril, and Quinapril.

14 Claims, No Drawings

METHOD FOR PREPARING OPTICALLY ACTIVE HOMOPHENYLALANINE AND ESTERS THEREOF USING LIPASE FROM WHEAT GERM OR *CANDIDA LIPOLYTICA*

FIELD OF THE INVENTION

The present invention relates to a method for the preparation of optically active D-homophenylalanine and its esters. More specifically, the present invention relates to the enantioselective synthesis of D-homophenylalanine, which is an important starting material for many important clinical drugs, such as Enalapril, Lisinopril, and Quinapril, used in the treatment of hypertension and congestive heart failure.

BACKGROUND OF THE INVENTION

D-homophenylalanine, which is represented by the following formula:

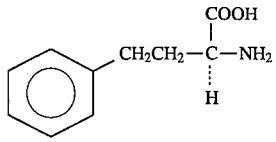

is an important starting material for anti-hypertensive drugs such as Enalapril, Lisinopril, and Quinapril. It has been reported that the chirality of $C_2$ is the homophenylalanine moiety of Enalapril is very important to its biological activities of angiotensin-converting enzyme inhibition; change of the chirality from the S (D) to R (L) configuration led to a $7 \times 10^2$-fold decrease of the converting enzyme inhibitory activities of Enalapril.

In this endeavor, D-homophenylalanine is first converted to ethyl ester of D-homophenylalanine, which is represented by the following formula:

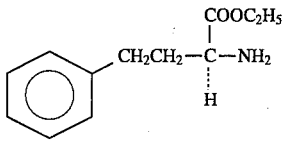

From the D-homophenylalanine ethyl ester, Enalapril, Lisinopril, and Quinapril are synthesized. These anti-hypertensive drugs are represented by the following formulas:

Enalapril:

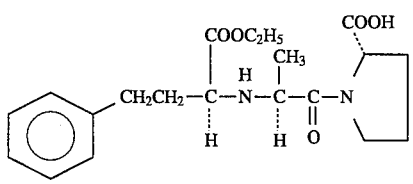

-continued
Quinapril:

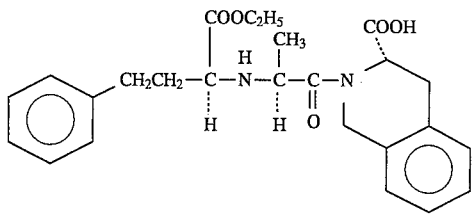

Lisinopril:

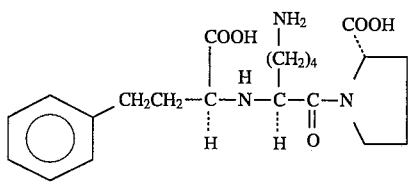

A very significant potential market is expected for the drugs related to D-homophenylalanine (including the Enalapril, Lisinopril, and Quinapril mentioned above). Therefore, there exists enormous economic incentive for the development of cost-effective processes for the production of optically active D-homophenylalanine.

In Japan Pat. App. JP 86-205850, it is disclosed a method for the preparation of optically active L-homophenylalanine by optical resolution via diastereomeric salts of racemic acetylhomophenylalanine. In JP 86-205850, optically active PhCH2CH2CH(NH2)CO2H is prepared by treatment of N-acetyl-DL-homophenylalanine with optically active PhCHMeNH2 in a solvent to prepare a solution containing two diastereomeric salts, from which a sparingly solution salt is separated, decomposed, and hydrolyzed. One of the disadvantages of the JP 86-205850 is the very high cost involved.

In Japan Pat. App. JP 86-291480, it is disclosed a method for the preparation of optically active D-homophenylalanine by resolution of DL-homophenylalanine, in which D-(−)-Mandelic acid and DL-homophenylalanine were dissolved in an aqueous alcohol solution, then the solution was cooled with crystalline D-(−)-Mandelic acid and L-homophenylalanine salts. The JP 86-291480 process also involves relatively high cost.

Syldatk, C., et al, in an article entitled: "Biotechnological Production of Unnatural L-Amino Acids from D,L-5-Monosubstituted Hydantoins," Biotech. Letters, Vol. 14, No. 2, pp. 105–110 (February, 1992), disclosed a method for the bioconversion of D,L-5-β- and D,L-5-β-naphthylmethylhydantoin to their corresponding L-amino acids using besting cells of *Arthrobacter sp.* (DSM 3745). Similar techniques were also disclosed in JP 87-279147 and JP 89-97523. JP-89-97523 discloses a method for manufacturing D-homophenylalanine by treating 5-benzylmethylhydantoin with Pseudomonas, Achromobacter, Alcaligenes, Serratia, Aspergillus, Rhizomucor, or D-hydantoin hydrolase from the microorganisms. *P. testosteroni* ATCC 11996 was cultured in a medium containing glucose, yeast extract, polypeptone, NaCl and 5-benzylmethylhydantoin at 26° C. for 48 hours, then centrifuged. The bacteria was treated with 1% 5-benzylmethylhydantoin in phosphate buffer at 37° C. for 72 hours to produce 96.5 μg optically pure D-homophenylalanine per ml. One of the main disadvantages of the bioconversion processes is that the microorganisms are very process specific, and it often involves a very tedious undertaking to screen and identify all the microorganism candidates that may work.

Tseng, Tsung-Chin, et al, in an article entitled: "Enantioselective Synthesis of N-[(S)-Ethoxycarbonyl-3-phenyl-propyl]-L-alanyl-L-proline from Chiral Synthon Prepared Enzymatically; A Practical Method for Large-Scale Synthesis," J. of the Chinese Chem. Soc., vol. 38, pp. 487–490 (1991), disclosed a process for stereospecific synthesis of Enalapril; the starting material, (R)-2-hydroxy-4-phenylbutyronitrile was prepared from lipase-catalyzed acetylation in dichloromethane solvent. This process is very slow; it took twelve days to complete the reaction.

Recently, several studies have demonstrated the possibility of using proteases as catalysts in organic solvents for the resolution of N-protected amino acids. For example, Chen, Shui-Tein, et al, in an article entitled: "Kinetic Resolution of N-Protected Amino Acid Esters in Organic Solvents Catalyzed by a Stable Industrial Alkaline Protease," Biotechnology letters, vol. 13, No. 11, pp. 773–778 (1991), it was disclosed that an industrial alkaline protease "Alcalase" was found to be usable as a catalyst for resolution of N-protected amino acids; only L-amino acid ester has been hydrolyzed. This method requires the extra steps of adding protective groups before the enzymatic reaction, and removing the protective groups after reaction. In another article entitled: "Enzymes in Organic Synthesis: Use of Subtilisin and a Highly Stable Mutant Derived from Multiple Site-Specific Mutations," J. Amer. Chem. Soc., vol. 112, pp. 945–953 (1990), Wong Chi-Huey disclosed the use of subtilisin 8350, a protease, in the enzymatic resolution of non-N-protected DL-amino acid esters by hydrolysis. One of the main disadvantages of this process is that the catalyst subtilisin 8350 causes the final product L-HPA to polymerize and form peptide.

More recently, in an article entitled: "Facile Optical Resolution of Amino Acid Esters Via Hydrolysis by an Industrial Enzyme in Organic Solvents," J. Chem. Tech. Biotechnol. vo. 59, pp. 61–65 (1994), Kijima T., disclosed that racemic amino acid esters can be optically resolved via hydrolysis in organic solvents by catalysis of an industrial alkaline, "Alcalase". In that article, it was found that, above 70% (v/v) water content, the e.e. (enantiometric excess) decreased sharply.

SUMMARY OF THE INVENTION

The primary object of the present invention is to develop a method for the production of optically active D-homophenylalanine (D-HPA), which can be subsequently used for the production of hypertensive drugs such as Enalapril, Lisinopril, and Quinapril. More specifically, the primary object of the present invention is to develop a method for the enantioselective synthesis of D-homophenylalanine which does not require an organic solvent and which can proceed with relatively fast reaction rates. Another object of the present invention is to develop a cost-effective method for the enantioselective hydrolysis of D-homophenylalanine esters which does not require a protective group for the amino acid. The method developed in the present invention can also be used in the optical resolution of other amino acids.

In the method disclosed in the present invention, DL-homophenylalanine ethyl ester (DL-HPAE) is reacted with a lipase in an aqueous solution without an organic solvent or any protective groups. The reaction, which is summarized below, is carried out in room temperature and normal pressure.

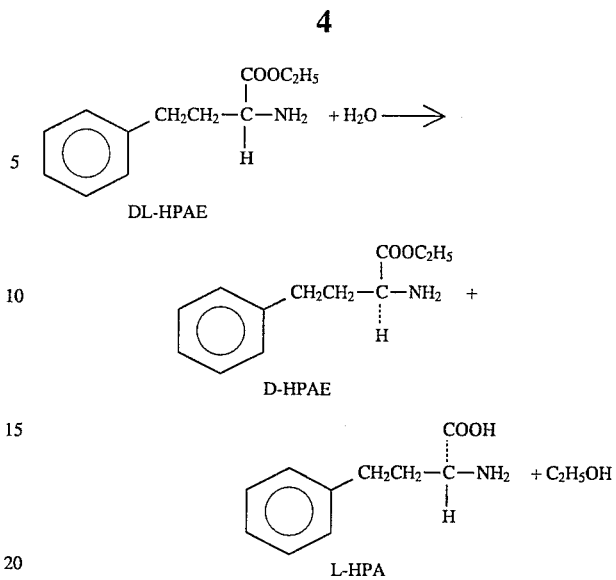

After the completion of the reaction, an extractant such as ethyl acetate is added to the reaction mixture which separates the reaction mixture into an upper layer and a lower layer. The upper layer contains D-HPAE in the organic solvent and the lower layer contains L-HPA in water. After separating the lower layer from the upper layer, the extractant, i.e., ethyl acetate, can be vaporized to obtain D-HPAE, which can be chemically hydrolyzed to obtain D-homophenylalanine.

DETAILED DESCRIPTION OF THE PREFERRED EMBODIMENT

The present invention discloses a method for the enantioselective synthesis of optically active D-homophenylalanine from DL-homophenylalanine ethyl ester. The D-homophenylalanine produced in the present invention can be subsequently used for the production of hypertensive drugs such as Enalapril, Lisinopril, and Quinapril. The method disclosed in the present invention does not require an organic solvent and which can proceed with relatively fast reaction rates; it also does not require a protective group for the amino acid. The method developed in the present invention can also be used in the optical resolution of other amino acids.

In the method disclosed in the present invention, DL-homophenylalanine ethyl ester (DL-HPAE) is reacted with a lipase or an acylase in an aqueous solution without an organic solvent or any protective groups. The enantioselective hydrolysis is carried out in room temperature and normal pressure as follows:

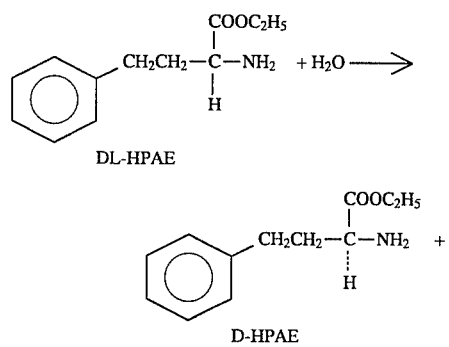

-continued

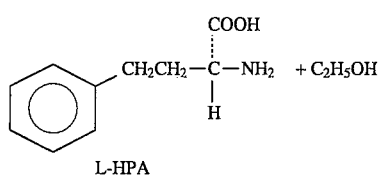

L-HPA

After the completion of the reaction, an extractant such as ethyl acetate is added to the reaction mixture which separates the reaction mixture into an upper layer and a lower layer. The upper layer contains D-HPAE in ethyl acetate and the lower layer contains L-HPA in water. After separating the lower layer from the upper layer, the extractant, i.e., ethyl acetate, can be vaporized to obtain D-HPAE, which can be chemically hydrolyzed to obtain D-homophenylalanine. L-HPA can be separated from the lower layer by adjusting its solution pH to about 6.3 to cause the precipitation thereof.

The present invention will now be described more specifically with reference to the following examples. It is to be noted that the following descriptions of examples, including the preferred embodiment of this invention, are presented herein for purposes of illustration and description, and are not intended to be exhaustive or to limit the invention to the precise form disclosed.

EXAMPLE 1

12 g of DL-homophenylalanine ethyl ester (DL-HPAE) was dissolved in 400 ml water, into which 8 g of Sigma 3126, a porcine pancreas lipase, was also added. The reaction mixture was stirred at room temperature while the pH was controlled using a pH controller in the range between 5.95 and 6.05. Samples were taken from the reaction mixture at varying time intervals. The reaction conversion and purity of the reaction product were measured by HPLC using an RP-18 column (Lichrospher, from Merck in Germany) and with a mobile phase consisting of 1:1 methanol/perchloric acid (pH 1.7) at an elution rate of 0.6 ml/min. The concentration of the eluent was detected at a wavelength of 215 nm.

The optical purity of the product was measured also by HPLC but using a Chiral Crownpak (+), or CR(+) column (by Diacel of Japan). The mobile phase in the optical purity measurement was 15:85 methanol/perchloric acid (pH 1.7), at an elution rate of 0.7 ml/min. The concentration of the eluent was detected at the same wavelength of 215 nm.

After the conversion from ester to acid reached a predetermined level (64%), the solution pH was adjusted to 2.0 to stop the reaction. Then, the solution pH was adjusted to 8.5 by adding 4N NaOH solution. Thereafter, 400 ml ethyl acetate was added which caused the reaction mixture to separate into two layers. The upper layer and the lower layer were separated by a simple decantation. The upper layer contained D-HPAE in ethyl acetate, which was vaporized to obtain about 3.2 g of the D-HPAE product, the e.e. value (enantiometric excess) was measured to be 95.1%. The D-HPAE was subsequently chemically hydrolyzed to obtain the optically active D-homophenylalanine, the e.e. value was measured to be 96.5%. The lower layer contained an aqueous solution of L-HPA, which was precipitated by adjusting the solution pH to 6.3.

EXAMPLES 2 THROUGH 29:

A number of lipases, acylases and esterases were used in the place of Sigma 3126, under similar reaction conditions as described in Example 1, above. All the enzymes listed in Table 1 are lipase, except Sigma 2156 and Sigma 8376, which are acylase, and Sigma 3128 and Sigma 9636, which are esterase. The results are summarized in Table 1. From Table 1, it is shown that Amano AP6 (from *Aspergillus niger*), Wako 120–01052 (from porcine pancreas), Serva 27930 (from *Rhizopus sp.*), Separacor (from *Pseudomonas sp.*), Sigma 3126 (from porcine pancreas), Sigma 3001 (from wheat germ), Fluka 62300 (from hog pancreas), Sigma 8376 (from porcine kidney) all showed e.e. values greater than 95%. Amano AY (from Candida cylindracea) showed an e.e. value of 82.4%. Other lipases, including Amano PS (From *Pseudomonas sp.*), Fluka 62301 (from *Aspergillus niger*) and Fluka 62310 (from *Rhizopus nineus*), also showed e.e. values greater 10%.

TABLE 1

| Enzyme | Enzyme Source | g/l | e.e. | Conv. (%) | Time (hr) | E |
| --- | --- | --- | --- | --- | --- | --- |
| Amano MY | Candida cylindracea | 8 | 0.038 | — | 5 | — |
| Amano AP6 | Aspergillus niger | 12 | 0.960 | 61.5 | 8 | 12.5 |
| Amano OF | Candida cylindracea | 8 | 0.012 | — | 5 | — |
| Amano L | Candida lipolytica | 8 | 0.028 | — | 5 | — |
| Amano D | Rhizopus delemer | 8 | 0.044 | — | 5 | — |
| Amano AY | Candida cylindracea | 12 | 0.824 | 76.9 | 12 | 3.7 |
| Amano AK | Pseudomonas sp. | 8 | 0.017 | — | 5 | — |
| Amano PS | Pseudomonas sp. | 40 | 0.924 | 72.4 | 3.5 | 6.1 |
| Amano MAP10 | Mucor meihei | 8 | 0.031 | — | 5 | — |
| Wako 120-01052 | Porcine pancreas | 8 | 0.959 | 67.3 | 1.5 | 9.7 |
| Serva 27930 | Rhizopus Sp. | 8 | 0.978 | 83.5 | 1.5 | 5.0 |
| Sepracor | Pseudomonas sp. | 8 | 0.975 | 67.5 | 1 | 10.8 |
| Novo lipozyme | Mucor miehei | 8 | 0.068 | — | 5 | — |
| Merck 24548 | Porcine pancreas | 4 | 0.102 | — | 5 | — |
| Sigma 3126 | Porcine pancreas | 10 | 0.951 | 64.0 | 1.5 | 11.4 |
| Sigma 1754 | Candida cylindracea | 8 | 0.086 | — | 5 | — |
| Sigma 3001 | Wheat germ | 8 | 0.950 | 85.0 | 7 | 4.0 |
| Sigma 4384 | Rhizopus arrhizus | 10 ml* | 0.018 | — | 5 | — |
| Sigma 2156 | Aspergillus Sp. | 8 | 0.038 | — | 5 | — |
| Sigma 8376 | Porcine kidney | 8 | 0.952 | 65.7 | 2 | 10.2 |
| Sigma 3128 | Porcine liver | 8 ml* | 0.001 | — | 5 | — |
| Sigma 9636 | Rabbit liver | 8 ml* | 0.344 | — | 5 | — |
| Fluka 62300 | Hog pancreas | 8 | 0.968 | 67.8 | 1.5 | 10.0 |
| Fluka 62301 | Aspegilliis niger | 8 | 0.182 | — | 5 | — |
| Fluka 62303 | Candida lipolytica | 8 | 0.101 | — | 5 | — |

TABLE 1-continued

| Enzyme | Enzyme Source | g/l | e.e. | Conv. (%) | Time (hr) | E |
|---|---|---|---|---|---|---|
| Fluka 62304 | *Mucor Javaricus* | 10 | 0.091 | — | 5 | — |
| Fluka 62305 | *Rhizopus arrhizus* | 8 | 0.041 | — | 5 | — |
| Fluka 62308 | *Penicillium raqueforti* | 4 | 0.034 | — | 5 | — |
| Fluka 62310 | *Rhizopus nineus* | 8 | 0.151 | — | 5 | — |

In Examples 30 through 43 that follow, various esters of DL-HPA were reacted with porcine pancreas lipase or *Pseudomonas sp.* lipase. The reactions were carried out in 5 ml of 0.2M phosphate buffer solution (pH 7.0) with 20 g/l of substrate and 50 mg (i.e., 10 g/l) of porcine pancreas lipase or 200 mg (i.e., 40 g/l) of *Pseudomonas sp.* lipase, at a reaction temperature of 30° C. The measured results indicate excellent e.e. values in all cases. In these examples, the esters of DL-HPA are represented by the following general formula:

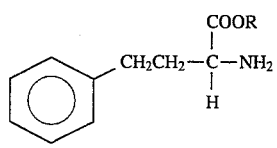

wherein R can be one of the following:

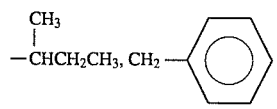

The cases using the ethyl ester of DL-homophenylalanine have been shown in the previous examples.

EXAMPLES 30 AND 31

In Example 30, a 20 g/l solution of DL-homophenylalanine methyl ester was prepared in a 0.2M phosphate buffer (pH 7.0). Then 10 g/l of a porcine pancreas lipase Sigma 3126 was also added. The mixture was caused to react at 30° C. The reaction conversion was measured by HPLC using an RP-18 column with a mobile phase consisting of 40:60 methanol/perchloric acid (pH 1.7) at an elution rate of 0.6 ml/min. The concentration of the eluent was detected at a wavelength of 215 nm. The optical purity of the product was measured using the CR(+) column with a mobile phase containing 15:85 methanol/perchloric acid (pH 1.7), at an elution rate of 0.7 ml/min. The concentration of the eluent was detected at the same wavelength of 215 nm. After 120 minutes, the reaction conversion was measured to be at 61.5%, and the e.e. value for the D-homophenylalanine and its methyl ester was measured to be 94.4%.

In Example 31, the porcine pancreas lipase Sigma 3126 was replaced with *Pseudomonas sp.* lipase at a concentration of 40 g/l. Under the same reaction conditions, the reaction conversion was measured to be 53.9%, and the e.e. value for the D-homophenylalanine and its methyl ester was measured to be 18.8%, after 200 minutes.

EXAMPLES 32 AND 33

In Example 32, a 20 g/l solution of DL-homophenylalanine n-propyl ester was prepared in a 0.2M phosphate buffer (pH 7.0). Then 10 g/l of a porcine pancreas lipase Sigma 3126 was also added. The mixture was caused to react at 30° C. The reaction conversion was measured by HPLC using an RP-18 column with a mobile phase consisting of 50:50 methanol/perchloric acid (pH 1.7) at an elution rate of 0.6 ml/min. The concentration of the eluent was detected at a wavelength of 215 nm. The remaining D-ester was extracted using ethyl acetate then hydrolyzed using 1N sodium hydroxide. The optical purity of the D-homophenylalanine was measured using the same procedure as described in Example 30, using a CR(+) HPLC column. After 80 minutes, the reaction conversion was measured to be 67.4%, and the e.e. value for the D-homophenylalanine and its n-propyl ester was measured to be 94.2%.

In Example 33, the porcine pancreas lipase Sigma 3126 was replaced with *Pseudomonas sp.* lipase at a concentration of 40 g/l. Under the same reaction conditions, the reaction conversion was measured to be 76.7%, and the e.e. value for the D-homophenylalanine and its n-propyl ester was measured to be 98.1%, after 60 minutes.

EXAMPLES 34 THROUGH 37

In Example 34, a 20 g/l solution of DL-homophenylalanine isopropyl ester was prepared in a 0.2M phosphate buffer (pH 7.0). Then 10 g/l of a porcine pancreas lipase Sigma 3126 was also added. The mixture was caused to react at 30° C. The reaction conversion was measured by HPLC using an RP-18 column with a mobile phase consisting of 55:45 methanol/perchloric acid (pH 1.7) at an elution rate of 0.6 ml/min. The concentration of the eluent was detected at a wavelength of 215 nm. The remaining D-ester was extracted using ethyl acetate then hydrolyzed using 1N sodium hydroxide. The optical purity of the D-homophenylalanine was measured using the same procedure as described in Example 30, using a CR(+) HPLC column. After 45 minutes, the reaction conversion was measured to be 53.3%, and the e.e. value for the D-homophenylalanine and its isopropyl ester was measured to be 93.0%.

In Example 35, the porcine pancreas lipase Sigma 3126 was replaced with *Pseudomonas sp.* lipase at a concentration of 40 g/l. Under the same reaction conditions, the reaction conversion was measured to be 61.3 %, and the e.e. value for the D-homophenylalanine and its isopropyl ester was measured to be 99.9%, after 240 minutes.

In Example 36, the porcine pancreas lipase Sigma 3126 was replaced with *Rhizopus sp.* lipase at a concentration of 10 g/l. Under the same reaction conditions, the reaction conversion was measured to be 85.7%, and the e.e. value for the D-homophenylalanine and its isopropyl ester was measured to be 80.9% after 115 minutes.

In Example 37, the porcine pancreas lipase Sigma 3126 was replaced with *Aspergillus niger* lipase at a concentration of 120 g/l. Under the same reaction conditions, the reaction conversion was measured to be 60.5%, and the e.e. value for the D-homophenylalanine and its isopropyl ester was measured to be 76.8%, after 300 minutes.

EXAMPLES 38 AND 39

In Example 38, a 20 g/l solution of DL-homophenylalanine n-butyl ester was prepared in a 0.2M phosphate buffer (pH 7.0). Then 10 g/l of a porcine pancreas lipase Sigma 3126 was also added. The mixture was caused to react at 30° C. The reaction conversion was measured by HPLC using an RP-18 column with a mobile phase consisting of 60:40 methanol/perchloric acid (pH 1.7) at an elution rate of 0.6 ml/min. The concentration of the eluent was detected at a wavelength of 215 nm. The remaining D-ester was extracted using ethyl acetate then hydrolyzed using 1N sodium hydroxide. The optical purity of the D-homophenylalanine was measured using the same procedure as described in Example 30, using a CR(+) HPLC column. After 90 minutes, the reaction conversion. was measured to be 62.5%, and the e.e. value for the D-homophenylalanine and its n-butyl ester was measured to be 97.8%.

In Example 39, the porcine pancreas lipase Sigma 3126 was replaced with *Pseudomonas sp.* lipase at a concentration of 40 g/l. Under the same reaction conditions, the reaction conversion was measured to be 67.2%, and the e.e. value for the D-homophenylalanine and its n-butyl ester was measured to be 95.4%, after 90 minutes.

EXAMPLES 40 AND 41

In Example 40, a 20 g/l solution of DL-homophenylalanine sec-butyl ester was prepared in a 0.2M phosphate buffer (pH 7.0). Then 10 g/l of a porcine pancreas lipase Sigma 3126 was also added. The mixture was caused to react at 30° C. The reaction conversion was measured by HPLC using an RP-18 column with a mobile phase consisting of 60:40 methanol/perchloric acid (pH 1.7) at an elution rate of 0.6 ml/min. The concentration of the eluent was detected at a wavelength of 215 nm. The remaining D-ester was extracted using ethyl acetate then hydrolyzed using 1N sodium hydroxide. The optical purity of the D-homophenylalanine was measured using the same procedure as described in Example 30, using a CR(+) HPLC column. After 180 minutes, the reaction conversion was measured to be 60.2%, and the e.e. value for the D-homophenylalanine and its secbutyl ester was measured to be 90.5%.

In Example 41, the porcine pancreas lipase Sigma 3126 was replaced with *Pseudomonas sp.* lipase at a concentration of 40 g/l. Under the same reaction conditions, the reaction conversion was measured to be 61.4%, and the e.e. value for the D-homophenylalanine and its sec-butyl ester was measured to be 93.1%, after 240 minutes.

EXAMPLES 42 AND 43

In Example 42, a 20 g/l solution of DL-homophenylalanine benzyl ester was prepared in a 0.2M phosphate buffer (pH 7.0). Then 10 g/l of a porcine pancreas lipase Sigma 3126 was also added. The mixture was caused to react at 30° C. The reaction conversion was measured by HPLC using an RP-18 column with a mobile phase consisting of 70:30 methanol/perchloric acid (pH 1.7) at an elution rate of 0.6 ml/min. The concentration of the eluent was detected at a wavelength of 215 nm. The remaining D-ester was extracted using ethyl acetate then hydrolyzed using 1N sodium hydroxide. The optical purity of the D-homophenylalanine was measured using the same procedure as described in Example 30, using a CR(+) HPLC column. After 150 minutes, the reaction conversion was measured to be 28.9%, and the e.e. value for the D-homophenylalanine and its benzyl ester was measured to be 33.4%.

In Example 43, the porcine pancreas lipase Sigma 3126 was replaced with *Pseudomonas sp.* lipase at a concentration of 40 g/l. Under the same reaction conditions, the reaction conversion was measured to be 62.9%, and the e.e. value for the D-homophenylalanine and its benzyl ester was measured to be 57.0%, after 200 minutes.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A method for preparing optically active homophenylalanine and esters thereof, comprising the steps of:
   (a) preparing a reaction mixture containing a DL-homophenylalanine ester and an enzyme, which is selected from the group consisting of wheat germ lipase and *Candida lipolytica* lipase, in an aqueous solution, wherein said DL-homophenylalanine ester is represented by the following general formula:

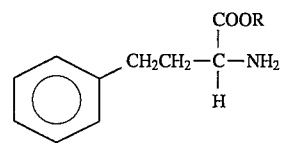

where R is selected from the group consisting of:
—$CH_3$, —$CH_2CH_3$, —$CH_2CH_2CH_3$,

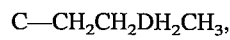

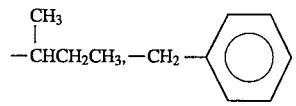

(b) reacting said reaction mixture at room temperature; and
   (c) using an extractant to separate the reacted reaction mixture into an upper layer, which contains an optically active D-homophenylalanine ester, and a lower layer, which contains L-homophenylalanine.

2. A method for preparing optically active homophenylalanine and esters thereof according to claim 1 which further comprises the step of chemically hydrolyzing said optically active D-homophenylalanine ester to obtain optically active D-homophenylalanine.

3. A method for preparing optically active homophenylalanine and esters thereof according to claim 1 wherein said enzyme is wheat germ lipase.

4. A method for preparing optically active homophenylalanine and esters thereof according to claim 1 wherein said enzyme is *Candida lipolytica* lipase.

5. A method for preparing optically active homophenylalanine and esters thereof according to claim 1 wherein said extractant is ethyl acetate.

6. A method for preparing optically active homophenylalanine and esters thereof according to claim 1 wherein said reaction is conducted at a pH of between 4 and 10.

7. A method for preparing optically active homophenylalanine and esters thereof according to claim 1 wherein said reaction is stopped by adjusting the solution pH to less than 4.

8. A method for preparing optically active homophenylalanine and esters thereof according to claim 1 wherein said DL-homophenylalanine ester does not contain any protective group on the amine.

9. A method for preparing optically active homophenylalanine and esters thereof according to claim 2 wherein said enzyme is wheat germ lipase.

10. A method for preparing optically active homophenylalanine and esters thereof according to claim 2 wherein said enzyme is *Candida lipolytica* lipase.

11. A method for preparing optically active homophenylalanine and esters thereof according to claim 2 wherein organic extractant is ethyl acetate.

12. A method for preparing optically active homophenylalanine and esters thereof according to claim 2 wherein said reaction is conducted at a pH of between 4 and 10.

13. A method for preparing optically active homophenylalanine and esters thereof according to claim 2 wherein said reaction is stopped by adjusting the solution pH to less than 4.

14. A method for preparing optically active homophenylalanine and esters thereof according to claim 2 wherein said DL-homophenylalanine ester does not contain any protective group on the amine.

* * * * *